United States Patent
Persson et al.

(10) Patent No.: US 9,921,189 B2
(45) Date of Patent: Mar. 20, 2018

(54) SENSOR UNIT FOR ULTRA SONIC SOUND WAVE COMMUNICATION

(71) Applicant: ATLAS COPCO INDUSTRIAL TECHNIQUE AB, Stockholm (SE)

(72) Inventors: Erik Vilhelm Persson, Solna (SE); Björn Gustav Undén, Enskede (SE)

(73) Assignee: Atlas Copco Industrial Technique AB, Stockholm (SE)

( * ) Notice: Subject to any disclaimer, the term of this patent is extended or adjusted under 35 U.S.C. 154(b) by 231 days.

(21) Appl. No.: 14/786,437

(22) PCT Filed: Apr. 30, 2014

(86) PCT No.: PCT/EP2014/058834
§ 371 (c)(1),
(2) Date: Oct. 22, 2015

(87) PCT Pub. No.: WO2014/180731
PCT Pub. Date: Nov. 13, 2014

(65) Prior Publication Data
US 2016/0061782 A1 Mar. 3, 2016

(30) Foreign Application Priority Data
May 7, 2013 (SE) .................................. 1350554-0

(51) Int. Cl.
*G01N 29/22* (2006.01)
*G01L 5/24* (2006.01)
(Continued)

(52) U.S. Cl.
CPC ........... *G01N 29/225* (2013.01); *B25B 23/14* (2013.01); *B25B 23/1425* (2013.01); *G01L 5/24* (2013.01);
(Continued)

(58) Field of Classification Search
CPC ................. G01N 29/225; G01N 29/07; G01N 2291/023; G01N 2291/011;
(Continued)

(56) References Cited

U.S. PATENT DOCUMENTS 5,058,439 A 10/1991 Carpenter
5,211,061 A * 5/1993 Goodwin ................ B23P 19/06
702/41
(Continued)

FOREIGN PATENT DOCUMENTS

EP 1570956 A1 9/2005

OTHER PUBLICATIONS

International Search Report (ISR) dated Jul. 31, 2014 issued in International Application No. PCT/EP2014/058834.

*Primary Examiner* — Paul West
*Assistant Examiner* — Xin Zhong
(74) *Attorney, Agent, or Firm* — Holtz Holtz & Volek PC

(57) ABSTRACT

A sensor unit for inducing and indicating ultra sonic sound waves in at least one threaded fastener by physical contact with an end surface thereof, wherein the sensor unit includes: a support casing, a sensor element with forward contact surface for engaging the fastener end surface and movable relative to the support casing between rest and active positions, and a bias spring between the support casing and the sensor element to urge the sensor element into the rest position as the sensor element is out of contact with the fastener end surface and to bias the contact surface of the sensor element into physical contact with the fastener end surface in the active position. The support casing includes a positioning socket, engaged by the sensor element in the rest position, having a non-cylindrical and non-circular cross sectional inner shape and congruent with an outer shape of the sensor element.

12 Claims, 2 Drawing Sheets

(51) Int. Cl.
*B25B 23/14* (2006.01)
*B25B 23/142* (2006.01)
*G01N 29/07* (2006.01)

(52) U.S. Cl.
CPC .............. *G01L 5/246* (2013.01); *G01N 29/07* (2013.01); *G01N 2291/011* (2013.01); *G01N 2291/023* (2013.01)

(58) Field of Classification Search
CPC ..... B25B 23/1425; B25B 23/14; G01L 5/246; G01L 5/0042; G01L 5/24; G01L 5/243
See application file for complete search history.

(56) References Cited

U.S. PATENT DOCUMENTS

| | | | |
|---|---|---|---|
| 7,188,549 B2 * | 3/2007 | Ohtake | ............... B25B 21/002 81/429 |
| 2005/0193869 A1 | 9/2005 | Ohtake et al. | |
| 2007/0140812 A1 | 6/2007 | Ohtake et al. | |

* cited by examiner

SENSOR UNIT FOR ULTRA SONIC SOUND WAVE COMMUNICATION

The invention relates to a sensor unit for ultra sonic sound wave communication. In particular, the invention concerns a sensor unit intended to be brought into physical contact with an end surface of a threaded fastener for inducing and indicating echoes of ultra sonic sound waves in a threaded fastener to thereby enable calculation of sound wave travel times through the fastener and from that the actual tension in the fastener.

A problem concerned with previous sensor arrangements for the above purpose is the difficulty to obtain a perfect alignment between the sensor and an end surface of a threaded fastener. Misalignment between the sensor and the threaded fastener end surface results in distortions of the sound wave signals being transferred between the threaded fastener end surface and the sensor, which in turn results in unreliable information of the sound wave travel times through the threaded fastener and, hence, an untrue information of the actual tension in the fastener.

It is an object of the invention to provide a sensor unit for inducing and indicating echoes of ultra sonic sound waves in threaded fasteners and by which misalignment between the sensor and an end surface of a threaded fastener is avoided.

It is a further object of the invention to provide an ultra sonic sound wave sensor unit for inducing and indicating echoes of ultra sonic sound waves in a threaded fastener and which comprises a support member and a sensor element, wherein the sensor element is movable relative to the support member and arranged to be self-aligned relative to an end surface of a threaded fastener when in physical contact with the latter.

It is a still further object of the invention to provide an ultra sonic sound wave sensor unit for inducing and indicating echoes of ultra sonic sound waves in a threaded fastener, wherein the sensor unit comprises a support member and a sensor element which is movable relative to the support member to obtain self-alignment with an end surface of the threaded fastener when in physical contact with the latter and to resume a well defined rest position when out of contact with the threaded fastener end surface.

Other objects and advantages of the invention will appear from the specification and claims.

Preferred embodiments of the invention are described below with reference to the accompanying drawings.

In the drawings

Figure 1:
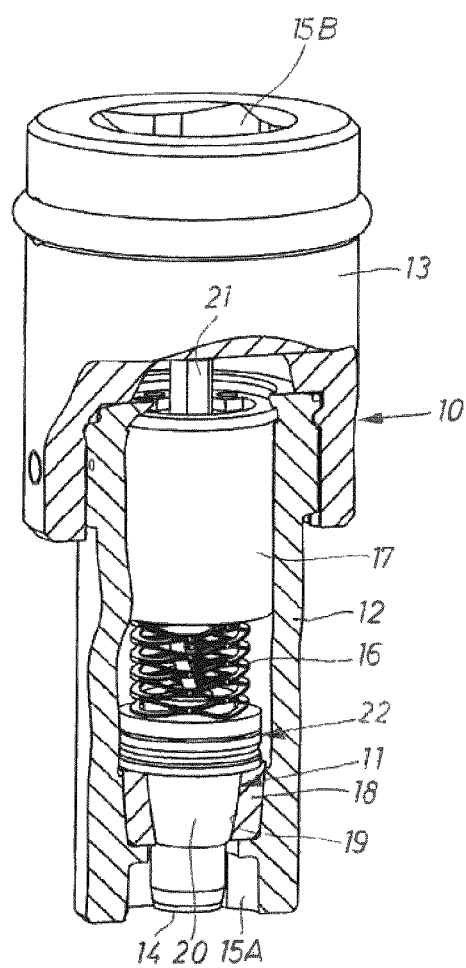
FIG. 1 shows, partly in section, a side view of a sensor unit according to the invention.

The sensor unit illustrated in the drawings comprises a tubular support casing 10 and a sensor element 11 movably supported relative to the support casing 10. The support casing 10 consists of a forward support sleeve 12 and a rear connection piece 13, whereof the forward support sleeve 12 is formed with a hexagonal socket portion 15A intended for torque transferring connection to a threaded fastener to be tightened, and the rear connection piece 13 is formed with an inner square portion 15B for connection to a wrench output shaft. Accordingly, the sensor unit is intended to be attached to the output shaft of a wrench, manually or power operated, wherein the sensor element 11 is connected to a non-illustrated operation control unit via wiring through the wrench. Since this is not a part of the invention it will not be described in further detail. However, the sensor element 11 is connected to wiring 21 which extends through the support sleeve 12 and is connected to a non-illustrated contact in the connection piece 13. This contact is intended to be engaged by a corresponding contact on the output shaft of a tightening wrench.

As well documented in prior art sensor elements for this purpose are of a piezo electric type and arranged to generate and induce ultra sonic sound waves into a threaded fastener element and also to pick up echoes of such induced sound waves reflected at the opposite end of the fastener. Accordingly, the sensor element 11 is able to transform electrical signals delivered by the operation control unit into sound waves, and vice versa to transform sound wave echoes into electrical signals. The operation control unit by which sound wave generating signals are delivered to and received from the sensor element 11 is arranged to establish the travel time of the sound waves through the fastener element and to calculate the actual tension in the fastener based on the established travel time.

The sensor element 11 has a forward contact surface 14 to be applied against an end surface of a threaded fastener, preferably the head of the fastener, wherein the sensor element 11 is axially movable relative to the support casing 10 between a forward rest position and a rear active position against the action of a bias spring 16. The spring 16 consists of a pile of spring washers and has a quite weak characteristic for avoiding a too heavy contact pressure on the sensor element 11 relative to a threaded fastener when compressed in its active position. The spring 16 is supported at its rear end by a tubular guide member 17 mounted inside the forward support sleeve 12.

Figure 3:
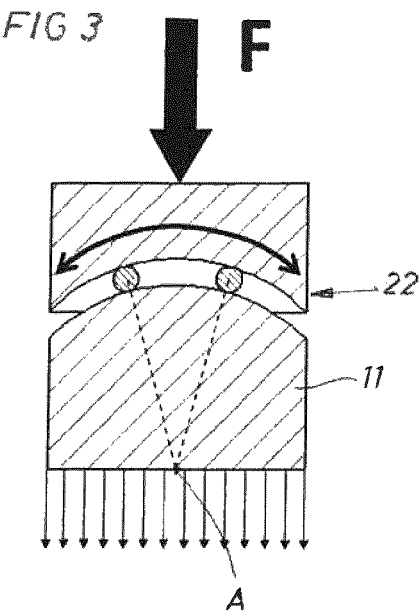
FIG. 3 shows a schematic illustration of the thrust bearing arrangement.

Between the bias spring 16 and the sensor element 11 there is provided a spherical thrust bearing 22 which has the function of allowing a certain tilting movement of the sensor element 11 when in contact with a fastener end surface which is not absolutely 90 degree perpendicular to the axial direction. Thereby, the sensor element 11 is facilitated to adapt to the end surface of a fastener. As illustrated in FIG. 3, the spherical thrust bearing 22 is arranged to compensate for occurring uneven contact pressure between the contact surface 14 of the sensor element 11 and the end surface of a fastener so as to have the axial force F applied to the sensor element 11 via the spring 16 distributed evenly over the contact surface 14. An evenly distributed contact pressure between the contact surface 14 and the end surface of a fastener is essential in getting a correct transfer of sound waves and having reliable signals indicating echoes of the reflected sound waves in the fastener. In order to avoid undesired lateral forces on the sensor element 11 the centre of tilting A of the thrust bearing 22 is located at or in front of the contact surface 14, which means that no lateral components of the axial application force F forces will be created in a tilted position of the sensor element 11. See FIG. 3.

Figure 2A:
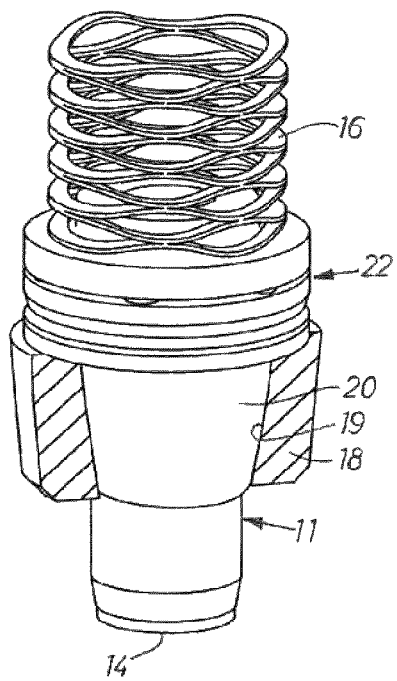
FIG. 2A shows on a larger scale a section of the sensor unit in FIG. 1 with the sensor element occupying its rest position.
Figure 2B:
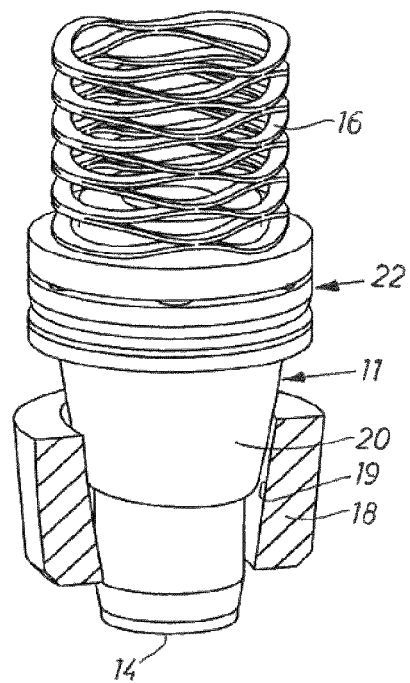
FIG. 2B shows a similar view as in FIG. 2A but with the sensor element in its active position.

The support sleeve 12 is provided with a ring shaped positioning socket 18 to be engaged by the sensor element 11 in its rest position, i.e. when the sensor unit is out of contact with any threaded fastener. The positioning socket 18 has a non-cylindrical, preferably conical surface inner surface 19 with a non-circular cross section, preferably an oval cross section, and the sensor element 11 is formed with an outer envelope surface 20 congruent with the inner surface 19 of the positioning socket 18 to match the latter and to guarantee an accurately positioned of the sensor element 11 relative to the support sleeve 12 in the rest position. When an axial force F is applied on the support casing 10 for applying a contact pressure between the sensor element 11 and a fastener end surface the sensor element 11 is pushed rearwards against the bias force of the spring 16, thereby leaving its rest position defined by the positioning socket 18. See FIG. 2B. Now, the sensor element 11 is free to move not only in its axial direction but also in limited rotational directions and in tilting directions so as to allow self-adaptation of the contact surface 14 of the sensor element 11 to the end surface of a threaded fastener. A perfect contact and alignment between the contact surface 14 and the end surface of a threaded fastener is very important for obtaining a true and distortion free sound wave transfer between the fastener and the sensor element 11, and hence a distortion free electrical signal to be transferred to the operation control unit. A further measure taken to ensure a distortion free signal transfer between the sensor element 11 and the end surface of the threaded fastener is the provision of a thin layer of a resinous resilient material on the contact surface 14 of the sensor element 11. This layer of a resilient material is thick enough to avoid direct metallic contact between the two surfaces to prevent irregularities in the interface contact between the sensor element 11 and a fastener end surface, but thin enough not to dampen out the transferred sound waves too much. A few tenth of a millimeter in thickness works well. This is a well known technique per se and is not illustrated in further detail.

In operation, the sensor unit is connected to a torque delivering wrench via the rear connection piece 13 and is brought into contact with a threaded fastener as the forward support sleeve 12 is applied on the head of a fastener element to be tightened. During a tightening process or after a completed tightening process ultra sonic sound waves are induced in the fastener by the sensor element 11, and echoes of sound waves reflected at the opposite end of the fastener element will be received by the sensor element 11 and sent to the operation control unit in the form of electrical signals. The sensor unit is connected to a non-illustrated operation control unit for measuring the travel time of the induced and reflected sound waves, and from that the actual tension in the threaded fastener may be calculated. This is a well known technique and is therefore not described in further detail.

An operation cycle commences by attaching the sensor unit to a tightening wrench and applying it on the head of a threaded fastener, whereby an axial force is applied on the sensor unit to urge the contact surface 14 of the sensor element 11 against the end surface of the fastener. This results in a certain compression of the bias spring 16 and a rearward displacement of the sensor element 11 in relation to the support casing 10 and the position defining positioning socket 18. As the sensor element 11 is out of engagement with the positioning socket 18 it is free to move in a number of directions, which means, apart from its axial movement, a limited freedom to rotate with respect to its longitudinal direction, as well as to tilt. The spherical thrust bearing 22 ensures that any occurring tilting movement of the sensor element 11 may be performed without undesired lateral forces being generated. The sensor element 11 is now able to be self-adapted in relation to the fastener end surface to thereby avoid any misalignment between the contact surface 14 of the sensor element 11 and the end surface of the threaded fastener, and hence avoid undesired signal distortions.

When the ultra sonic sound wave travel time measuring operation is completed the wrench and the sensor unit are lifted off the threaded fastener which results in a forward movement of the sensor element 11 relative to the support casing 10, whereby the sensor element 11 will resume its engagement with the positioning socket 18. As the sensor element 11 is fully introduced in the positioning socket 18 the cooperation between the conical and non-circular surfaces 19 of the positioning socket 18 and the congruent envelope surface 20 of the sensor element 11 will now define the rest position of the sensor element 11 with respect to all directions of freedom, i.e. axial, angular, and tilting movements. By this arrangement, the sensor element 11 will always resume a well defined rest position which also becomes a well defined starting point for a succeeding ultra sonic sound wave travel time measuring operation.

In the active position of the sensor element 11 all of the directions of freedom of movement of the sensor element 11 are limited to a certain extent but are big enough to allow a proper adaptation of the sensor element 11 to the end surface of a threaded fastener. The freedom of rotation for instance is limited to 15-20 degrees so as to avoid damage to the wiring connected to the sensor element 11 to the contact element in the rear connection piece 13.

It is to be noted that the embodiments of the invention are not limited to the example described above but may be freely varied within scope of the claims. For instance, the cross sectional shape of the inner surface of the positioning socket 18 may be other than oval.

The invention claimed is:

1. A sensor unit for inducing and indicating ultra sonic sound waves in at least one threaded fastener by being brought into physical contact with an end surface of the at least one threaded fastener, wherein the sensor unit comprises:
   a support casing and a sensor element, said sensor element having a forward contact surface for engaging the end surface of the at least one threaded fastener and being movable relative to the support casing between a rest position and an active position, and
   a bias spring acting between the support casing and the sensor element to urge the sensor element into said rest position as the sensor element is out of contact with the at least one threaded fastener end surface and to bias the contact surface of the sensor element into physical contact with the at least one threaded fastener end surface in said active position,
   wherein the support casing comprises a positioning socket to be engaged by the sensor element in said rest position, said positioning socket having a non-cylindrical inner shape and non-circular cross sectional inner shape, and the sensor element has an outer shape congruent with said inner shape of said positioning socket, and
   wherein in the rest position, the sensor element is immovable in rotational and tilting positions relative to the support casing.

2. The sensor unit according to claim 1, wherein the inner shape of said positioning socket is conical and has an oval cross section.

3. The sensor unit according to claim 1, wherein a spherical thrust bearing is provided between the spring and the sensor element to facilitate tilting displacement and self-adaptation of the sensor element relative to the at least one threaded fastener end surface.

4. The sensor unit according to claim 2, wherein a spherical thrust bearing is provided between the spring and the sensor element to facilitate tilting displacement and self-adaptation of the sensor element relative to the at least one threaded fastener end surface.

5. The sensor unit according to claim 1, wherein the support casing comprises a rear connection piece and a forward support sleeve, and said positioning socket is located inside the support sleeve.

6. The sensor unit according to claim 2, wherein the support casing comprises a rear connection piece and a forward support sleeve, and said positioning socket is located inside the support sleeve.

7. The sensor unit according to claim 3, wherein the support casing comprises a rear connection piece and a forward support sleeve, and said positioning socket is located inside the support sleeve.

8. The sensor unit according to claim 4, wherein the support casing comprises a rear connection piece and a forward support sleeve, and said positioning socket is located inside the support sleeve.

9. The sensor unit according to claim 5, wherein said support sleeve comprises a socket portion for connection and application of a tightening torque to the at least one threaded fastener.

10. The sensor unit according to claim 6, wherein said support sleeve comprises a socket portion for connection and application of a tightening torque to the at least one threaded fastener.

11. The sensor unit according to claim 7, wherein said support sleeve comprises a socket portion for connection and application of a tightening torque to the at least one threaded fastener.

12. The sensor unit according to claim 8, wherein said support sleeve comprises a socket portion for connection and application of a tightening torque to the at least one threaded fastener.

* * * * *